US00PP11556P

United States Patent [19]

Tachibana et al.

[11] Patent Number: Plant 11,556

[45] Date of Patent: Oct. 10, 2000

[54] MANDEVILLA PLANT NAMED 'SUNMANDEHO'

[75] Inventors: Ryuichi Tachibana, Kawasaki; Kenichi Suzuki, Ibaraki; Yasunori Yomo, Yamanashi, all of Japan

[73] Assignee: Suntory Limited, Osaka, Japan

[21] Appl. No.: 09/159,087

[22] Filed: Sep. 22, 1998

[51] Int. Cl.[7] ..... A01H 5/00

[52] U.S. Cl. ..... Plt./232

[58] Field of Search ..... Plt./232

[56] References Cited

U.S. PATENT DOCUMENTS

| | | | |
|---|---|---|---|
| P.P. 8,479 | 11/1993 | Henny | Plt./232 |
| P.P. 8,842 | 7/1994 | Henny | Plt./232 |
| P.P. 9,117 | 4/1995 | Chirstensen | Plt./232 |
| P.P. 9,118 | 4/1995 | Petersen | Plt./232 |
| P.P. 10,095 | 11/1997 | Henny | Plt./232 |
| P.P. 10,329 | 4/1998 | Wells | Plt./232 |
| P.P. 10,413 | 5/1998 | Alston | Plt./232 |
| P.P. 10,611 | 9/1998 | Alston | Plt./232 |

*Primary Examiner*—Howard J. Locker
*Assistant Examiner*—Michelle Kizilkaya
*Attorney, Agent, or Firm*—Burns, Doane, Swecker & Mathis, L.L.P.

[57] ABSTRACT

A new and distinct variety of Mandevilla plant is provided that was created through controlled cross-breeding. The female parent was a *Mandevilla amabilis* 'Rose Giant' plant and the male parent was a *Mandevilla boliviensis* plant. The new variety exhibits a lianous growth habit and well tolerates heat. Attractive yellowish-white flowers having a vivid yellow throat are formed over an extended period of time. The flower petals curve outwards. Olive green leaves having an entire margin are formed. Plants of the new variety are well suited for growing in pots that are equipped with a support for climbing.

2 Drawing Sheets

BACKGROUND OF THE VARIETY

The present invention relates to a new and distinct variety of Mandevilla plant obtained from a crossing a *Mandevilla amabilis* 'Rose Giant' plant (♀) and a *Mandevilla boliviensis* plant (♂).

The Mandevilla is a popular plant and is used as a pot plant in the summer season or an indoor plant or a glasshouse plant. Only a limited number of varieties of Mandevilla plants are commercially available. Accordingly, this invention was aimed at obtaining a new variety having a large diameter flower, a white flower, and a long flowering duration.

Initially, 35 seedlings were obtained in the autumn of 1991, from crossing a 'Rose Giant' plant (non-patented in the United States) as female parent and a *Mandevilla boliviensis* plant (non-patented in the United States) as pollen parent. These 35 seedling were grown in a glasshouse and one seedling was selected in view of its flower size and flowering duration. The selected seedling was propagated by the use of cuttings, and was then grown as a trial in a planter from the summer of 1993 to the summer of 1995. Finally the selected seedling was examined using the similar parent varieties 'Rose Giant' and *Mandevilla boliviensis* for comparative purposes. As a result, it was concluded that this new Mandevilla is distinguishable from any other variety whose existence is known to us and is uniform and stable in its characteristics. This new variety has been named 'Sunmandeho'.

In the following description, the color-coding is in accordance with the R.H.S. Colour Chart of The Royal Horticultural Society, London, England. The color chart of The Japan Color Standard for Horticultural Plants (J.H.S. Color Chart) is also added for reference.

The *Mandevilla amabilis* 'Rose Giant' used as the female parent in the obtaining of this new variety 'Sunmandeho' is commercially available. The Mandevilla plant *Mandevilla amabilis* 'Rose Giant' also is presently maintained at the Hakushu Nursery Center of SUNTORY Ltd., at 2913-1 Torihara, Hakashu- cho, Kitakoma-gun, Yamanashiken, Japan. The main botanical characteristics of *Mandevilla amabilis* 'Rose Giant' are as follows:

Plant:
- *Growth habit*.—Lianous.

Stem:
- *Stem diameter*.—Medium (5.0–6.0 mm).
- *Stem color*.—Dark reddish brown (J.H.S. Color Chart No. 1009, R.H.S. Colour Chart No. 183A).
- *Shoot color*.—Vivid yellow green (J.H.S. Color Chart No. 3506, R.H.S. Colour Chart No. 144B).
- *Lenticel*.—Present.
- *Branching*.—Few.
- *Internode length*.—Long (10.0–17.0 cm).

Leaf:
- *Phyllotaxis*.—Opposite.
- *Whole shape of leaf*.—Oblong.
- *Shape of leaf apex*.—Mucronate.
- *Shape of leaf base*.—Cordate.
- *Leaf length*.—Medium (9.0–11.0 cm).
- *Leaf width*.—Narrow (5.0–7.0 cm).
- *Leaf thickness*.—Medium-thick (0.2–0.4 mm).
- *Color of immature leaf upper side*.—Moderate Olive green (J.H.S. Color Chart No. 3509, R.H.S. Colour Chart No. 147A).
- *Color of mature leaf upper side*.—Dark grayish olive green (J.H.S. Color Chart No. 3510, R.H.S. Colour Chart No. 139A).
- *Color of mature leaf reverse side*.—Moderate yellow green (J.H.S. Color Chart No. 3514, R.H.S. Colour Chart No. 147B).
- *Varieagation of mature leaf*.—Absent.
- *Gloss of mature leaf upper side*.—Medium.
- *Pubescence of mature leaf upper side*.—Present.
- *Pubescence of mature leaf reverse side*.—Present.
- *Leaf petiole length*.—Medium (0.8–1.0 cm).

*Leaf petiole diameter*.—Medium-thick (3.1–3.5 mm).
*Leaf petiole color*.—Brilliant yellow green (J.H.S. Color Chart No. 3504, R.H.S. Colour Chart No. 149B).
*Leaf abscission*.—Leaves fall when subjected to low temperature in late autumn.

Flower:
*Color of flower bud*.—Strong purplish pink (J.H.S. Color Chart No. 9504, R.H.S. Colour Chart No. 62B).
*Length of peduncle*.—Short-medium (0.6–0.9 cm).
*Peduncle color*.—Vivid yellow green (J.H.S. Color Chart No. 3506, R.H.S. Colour Chart No. 149A).
*Pedicel length*.—Medium-long (0.6–2.2cm).
*Length of inflorescence*.—Medium-long (6.0–7.0 cm).
*Width of inflorescence*.—Medium-broad (1.2–1.5 cm).
*Flower shape*.—Single.
*Flower form*.—Perfectly open.
*Flower facing direction*.—Horizontal to slanted upward.
*Diameter of flower*.—Medium (7.0.–10.0 cm).
*Flower height*.—Medium (7.0–0 9.0 cm).
*Floral tube length*.—Medium-long 5.0–5.5cm).
*Color of flower upper side*.—Deep purplish pink (J.H.S. Color Chart No. 9705, R.H.S. Colour Chart No. 155A).
*Color of inside surface of corolla throat*.—Yellowish white (J.H.S. Color Chart No. 2502, R.H.S. Colour Chart No. 155D).
*Color of flower outside*.—Deep purplish pink (J.H.S. Color Chart No. 9705, R.H.S. Colour Chart No. 55A).
*Overlapping of petals*.—Closed.
*Whole shape of petal lobe*.—Orbicular.
*Shape of petal lobe apex*.—Cuspidate.
*Curvature of petal*.—Outwardly curved.
*Waving of petal*.—Weak.
*Petal length*.—Long (4.5–5.5 cm).
*Petal width*.—Broad (5.5–6.0 cm).
*Petal number*.—Medium (5).
*Type of sepal*.—Open.
*Sepal length*.—Short-medium (1 .9–2.2 cm).
*Sepal width*.—Medium-broad (2.0–2.3 cm).
*Sepal color*.—Strong yellow green (J.H.S. Colour Chart No. 3507, R.H.S. Colour Chart No. 144A).
*Lobation of sepal*.—Medium.

Reproductive organs:
*Pistil*.—Present.
*Pistil number*.—1.
*Stamen number*.—5.
*Anther color*.—Bright yellow (J.H.S. Color Chart No. 2204, R.H.S. Colour Chart No. 15B).
*Anther appendage*—. Absent.

Physiological and ecological characteristics:
*Flower number*.—Many (5–9 per cluster).
*Flower fragrance*.—Absent-weak.
*Fertility*.—Absent.
*Leaf abscission*.—Medium.
*Flower abscission*.—Medium.
*Flowering time*.—Early.
*Flowering duration*.—Long (early June to late October in Japan).
*Cold tolerance*.—Low.
*Heat tolerance*.—High.
*Resistance to diseases*.—Medium.
*Resistance to pests*.—Medium.

The *Mandevilla boliviensis* plant used as pollen parent in obtaining this new variety 'Sunmandeho' is commercially available. This Mandevilla parent plant also is presently maintained at the Hakushu Nursery Center of SUNTORY Ltd., at 2913-1 Torihara, Hakushu-cho, Kitakomagun, Yamanashi-ken, Japan. The main botanical characteristics of the pollen parent, *Mandevilla boliviensis* are as follows:

Plant:
*Growth habit*.—Lianous.
*Stem diameter*.—Thin (2.5–4.7 mm).
*Stem color*.—Moderate yellow green (J.H.S. Color Chart No. 3513, R.H.S. Colour Chart No. 144B).
*Shoot color*.—Vivid yellow green (J.H.S. Color Chart No. 3506, R.H.S. Colour Chart No. 144B).
*Lenticel*.—Present.
*Branching*.—Medium.
*Internode length*.—Short (3.8–4.2 cm).

Leaf:
*Phyllotaxis*.—Opposite.
*Whole shape of leaf*.—Elliptic.
*Shape of leaf apex*.—Cuspidate.
*Shape of leaf base*.—Obtuse.
*Leaf length*.—Medium (8.8–10.5 cm).
*Leaf width*.—Narrow (3.6–4.5 cm).
*Leaf thickness*.—Medium (0.2–0.25 mm).
*Color of immature leaf upper side*.—Strong yellow green (J.H.S. Color Chart No. 3507, R.H.S. Colour Chart No. 144A).
*Color of mature leaf upper side*.—Dark olive green (J.H.S. Color Chart No. 3707, R.H.S. Colour Chart No. 144A).
*Color of mature leaf reverse side*.—Dark grayish olive green (J.H.S. Color Chart No. 3510, R.H.S. Colour Chart No. 139A).
*Variegation of mature leaf*.—Absent.
*Gloss of mature upper side*.—Medium-strong.
*Pubescence of mature leaf upper side*.—Absent.
*Pubescence of mature leaf reverse side*.—Absent.
*Leaf petiole length*.—Long (1.3–2.2 cm).
*Leaf petiole diameter*.—Thin-medium (2.0–2.2 mm).
*Leaf petiole color*.—Moderate yellow green (J.H.S. Color Chart No. 3513, R.H.S. Colour Chart No. 146C).
*Leaf abscission*.—Leaves fall when subject to low temperature in late autumn.

Flower:
*Color of flower bud*.—Pale yellow green (J.H.S. Color Chart No. 3502, R.H.S. Colour Chart No. 149D).
*Length of penducle*.—Medium-long (1.8–2.5 cm).
*Penducle color*.—Strong yellow green (J.H.S. Color Chart No. 3507, R.H.S. Colour Chart No. 144A).
*Pedicel length*.—Short-medium (0.4–0.7 cm).
*Length of inflorescence*.—Medium-long (5.5–7.2 cm).
*Width of inflorescence*.—Medium (0.9–1.1 cm).
*Flower shape*.—Single.
*Flower form*.—Perfectly open.
*Flower facing direction*.—Slanted upward.
*Diameter of flower*.—Small (5.5–7.0 cm).
*Diameter of flower*.—Medium (6.0–7.0 cm).
*Flower height*.—Medium (6.0–7.0 cm).
*Floral tube length*.—Medium (4.0–5 cm).
*Color of flower upper side*.—Yellowish white (J.H.S. Color Chart No. 2701, R.H.S. Colour Chart No. 155C).

*Color of inside surface of corolla throat.*—Vivid yellow (J.H.S. Color Chart No. 2205, R.H.S. Colour Chart No. 15A).
*Color of flower outside.*—Pale greenish yellow (J.H.S. Color Chart No. 2903, R.H.S. Colour Chart No. 2D).
*Overlapping of petals.*—Closed.
*Whole shape of petal lobe.*—Orbicular.
*Shape of petal lobe apex.*—Cuspidate.
*Curvature of petal.*—Inwardly curved.
*Waving of petal.*—Medium.
*Petal length.*—Short-medium (2.5–3.0 cm).
*Petal width.*—Narrow (2.5–2.7 cm).
*Petal number.*—Medium (5).
*Type of sepal.*—Slanted upwards.
*Sepal length.*—Medium-long (2.3–3.5 cm).
*Sepal width.*—Medium-broad (2.2–2.5 cm).
*Sepal color.*—Brilliant yellowish green (J.H.S. Color Chart No. 3505, R.H.S. Colour Chart No. 144C).
*Lobation of sepal.*—Shallow.

Reproductive organs:
*Pistil.*—Present.
*Pistil number.*—1.
*Stamen number.*—5.
*Anther color.*—Brilliant yellowish (J.H.S. Color Chart No. 2204, R.H.S. Colour Chart No. 15B).
*Anther appendage.*—Absent.

Physiological and ecological characteristics:
*Flower number.*—Few-medium (3–4 per cluster).
*Flower fragrance.*—Absent-weak.
*Fertility.*—Absent.
*Leaf abscission.*—Medium.
*Flower abscission.*—Medium.
*Flowering time.*—Early.
*Flowering duration.*—Long (Early June to early November in Japan).
*Cold tolerance.*—Low.
*Heat tolerance.*—High.
*Resistance to diseases.*—Medium.
*Resistance to pests.*—Medium.

This new variety of Mandevilla plant. 'Sunmandeho' was asexually reproduced by cuttings at the afore-mentioned Hakushu Nursery Center of SUNTORY Ltd., located at 2913-1 Torihara, Hakushu-cho, Kitakoma-gun, Yamanashi-ken, Japan, and the homogeneity and stability thereof were thereby confirmed.

SUMMARY OF THE NEW VARIETY

This new variety of Mandevilla plant possesses a lianous growth habit. The blooming period is early June to early November in Japan and the flowering duration is long. When growing conditions are above 18° C. flowering is substantially continuous. The flower diameter is large. Both surfaces of the petals are yellowish white and the inside surface of corolla throat is vivid yellow. The leaves are medium olive green and are hairless on both faces. The plant is highly tolerant to heat.

BRIEF DESCRIPTION OF THE PHOTOGRAPHS

DETAILED DESCRIPTION OF THE NEW VARIETY

Figure 1:
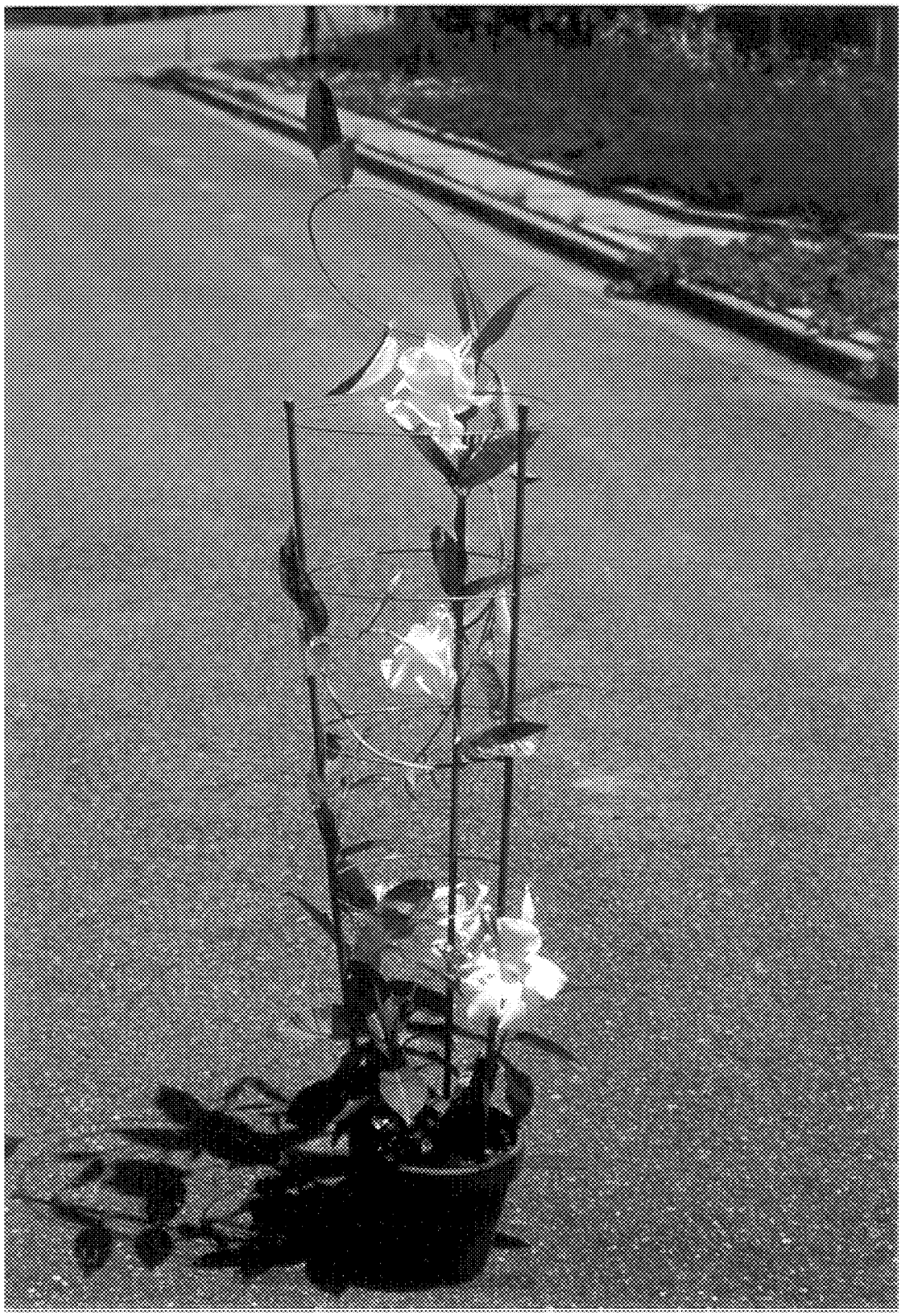
FIG. 1 is photograph of the new 'Sunmandeho' variety of Mandevilla plant when growing in a pot.
Figure 2:
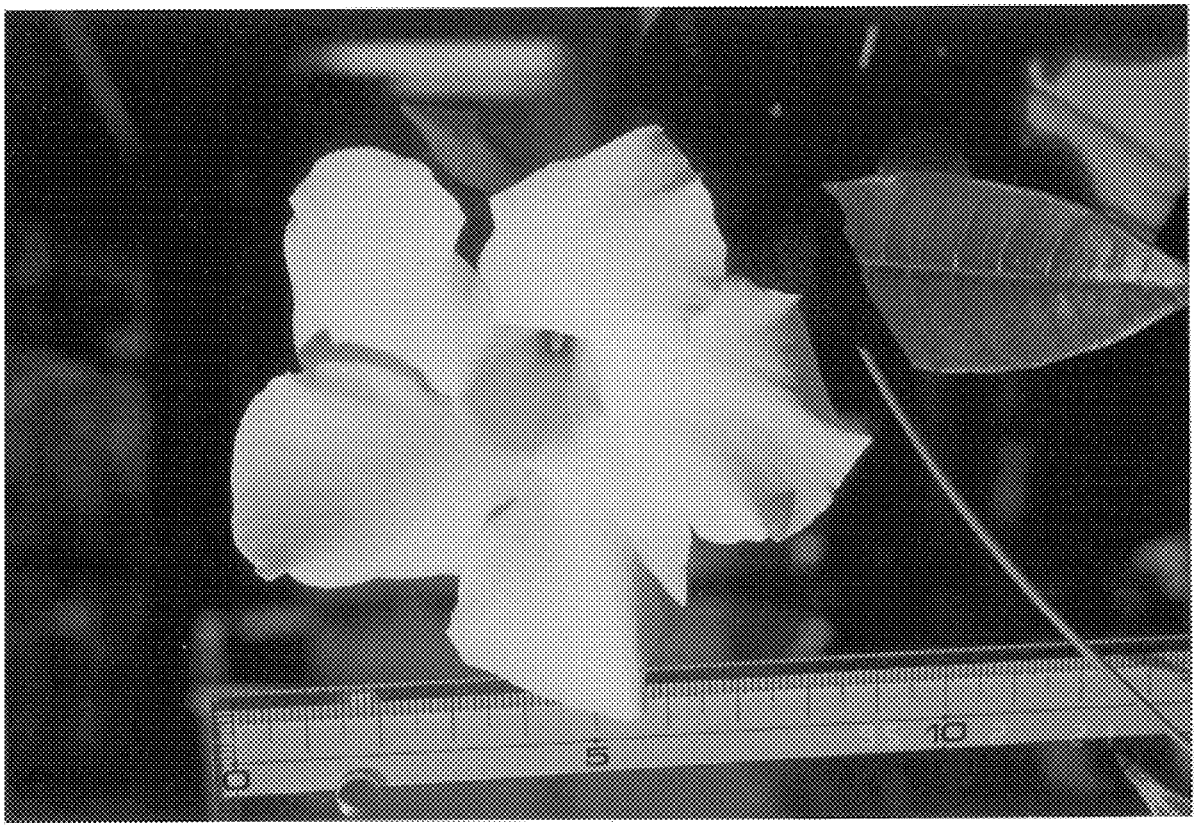
FIG. 2 is a closeup photograph of flower of the new 'Sunmandeho' variety of Mandevilla plant.

The botanical characteristics of the new. 'Sunmandeho' variety of Mandevilla plant are as follows:

Plant:
*Growth habit.*—Lianous.

Stem:
*Stem diameter.*—Thin-medium (4.–5.0 mm).
*Stem color.*—Gradually darkens on young stems from J.H.S. Color Chart No. 3505 (R.H.S. Colour Chart No. 149A) to J.H.S. Color Chart No. 3506 (R.H.S. Colour Chart No. 144B) to J.H.S. Color 3507 (R.H.S. Colour Chart No. 144A). Upon maturity is J.H.S. Color Chart No. 1610 (R.H.S. Colour Chart No. 167D).
*Shoot color.*—Brilliant yellow green (J.H.S. Color Chart No. 3505, R.H.S. Colour Chart No. 149A).
*Lenticel.*—Not visible.
*Branching.*—Few.
*Internode length.*—Medium (5.0–13.0 cm).

Leaf:
*Phyllotaxis.*—Opposite.
*Whole shape of leaf.*—Elliptic.
*Shape of leaf apex.*—Cuspidate.
*Shape of leaf base.*—Acute.
*Leaf length.*—Medium (8.0–11.0 cm).
*Leaf width.*—Narrow-medium (4.0–5.0 cm).
*Leaf thickness.*—Medium (0.2 mm).
*Leaf margin.*—Entire.
*Color of immature leaf upper side.*—Medium olive green (J.H.S. Color Chart No. 3508, R.H.S. Colour Chart No. 146A).
*Color of mature leaf upper side.*—Medium olive green (J.H.S. Color Chart No. 3508, R.H.S. Colour Chart No. 146A).
*Color of mature leaf reverse side.*—Medium yellow green (J.H.S. Color Chart No. 3513, R.H.S. Colour Chart No. 146C).
*Variegation of mature leaf.*—Absent.
*Gloss of mature leaf upper side.*—Medium-strong.
*Pubescence of mature leaf upper side.*—Absent.
*Pubescence of mature leaf reverse side.*—Absent.
*Leaf petiole length.*—Medium-long (1.3–1.5 cm).
*Leaf petiole diameter.*—Thin-medium (2.0–2.2 mm).
*Leaf petiole color.*—Brilliant yellow green (J.H.S. Color Chart No. 3504, R.H.S. Colour Chart No. 145B).
*Leaf abscission.*—Leaves fall when subjected to low temperatures in late autumn.

Flower:
*Color of flower bud.*—Light yellow green (J.H.S. Color Chart No. 3503, R.H.S. Colour Chart No. 149C).
*Length of flower bud.*—Medium-long (6.0–7.0 cm).
*Width of flower bud.*—Medium-broad (1.2–1.5 cm).
*Length of peduncle.*—Short-medium (0.5–0.9 cm).
*Penducle color.*—Strong yellow green (J.H.S. Color Chart No. 3512, R.H.S. Colour Chart No. 144B).
*Pedicel length.*—Medium-long (0.7–1.7 cm).
*Flower shape.*—Single.
*Flower form.*—Perfectly open.
*Flower facing direction.*—Horizontal to slanted upward.
*Diameter of flower.*—Large (10.0–11.0 cm).
*Flower height.*—Medium-high (7.0–9.0 cm).
*Floral tube length.*—Medium-long (5.0–5.5 cm).

*Color of flower upper side*.—Yellowish white (J.H.S. Color Chart No. 2901, R.H.S. Colour Chart No. 155C).
*Color of inside surface of corolla throat*.—Vivid yellow (J.H.S. Color Chart No. 2205, R.H.S. Colour Chart No. 15A).
*Color of flower outside*.—Yellowish white (J.H.S. Color Chart No. 2201, R.H.S. Colour Chart No. 158D).
*Overlapping of petals*.—Closed.
*Whole shape of petal lobe*.—Orbicular.
*Shape of petal lobe apex*.—Cuspidate.
*Curvature of petal*.—Outwardly curved.
*Waving of petal*.—Medium.
*Petal length*.—Long (4.5–5.5 cm).
*Petal width*.—Broad (5.5–6.0 cm).
*Petal number*.—Medium (5).
*Type of sepal*.—Open.
*Sepal length*.—Long (3.0–3.5 cm).
*Sepal width*.—Narrow (0.42 cm).
*Sepal color*.—Light yellow green (J.H.S. Color Chart No. 3503, R.H.S. Colour Chart No. 145B).
*Lobation of sepal*.—Medium.

Reproductive organs:
*Pistil*.—Present.
*Pistil number*.—1.
*Stamen number*.—5.
*Anther color*.—Brilliant yellow (J.H.S. Color Chart No. 2204, R.H.S. Colour Chart No. 15B).
*Anther appendage*.—Absent.

Physiological and ecological characteristics:
*Flower number*.—Medium (commonly 4–5 per cluster).
*Flower fragrance*.—Absent-weak.
*Fertility*.—Self fertile. Approximately 100 seeds commonly form in a single chambered fruit follicle that is approximately 10 to 15 mm in length.
*Leaf abscission*.—The leaves fall when subjected to low temperature in late autumn.
*Flower abscission*.—Medium. The flowers commonly last approximately 7 to 10 days on the plant.
*Flowering time*.—Early.
*Flowering duration*.—Long and substantially continuous (early June to early November in Japan). The individual blossoms commonly last 7 to 10 days on the plant.
*Cold tolerance*.—Low.
*Heat tolerance*.—High.
*Resistance to diseases*.—Medium.
*Resistance to pests*.—Medium.

This new variety of Mandevilla plant, 'Sunmandeho' is most suitable for potting in the summer season or for use as an indoor plant or as a glasshouse plant. This new variety exhibits a lianous growth habit and can be readily trained to grow on a wire or other upright support.

We claim:

1. A new and distinct variety of Mandevilla plant that exhibits:

(a) a lianous growth habit,
(b) forms attractive large yellowish-white flowers over an extended period of time having petals that curve outwards,
(c) displays medium olive green leaves, and
(d) well tolerates heat;

substantially as shown and described.

* * * * *